United States Patent
Pierrot et al.

(10) Patent No.: US 6,516,681 B1
(45) Date of Patent: Feb. 11, 2003

(54) FOUR-DEGREE-OF-FREEDOM PARALLEL ROBOT

(75) Inventors: Francois Pierrot, 120 Montee du Terral, 34430 Saint-Jean-de-Vedas (FR); Olivier Company, Gignac (FR); Tetsuro Shibukawa, Nagoya (JP); Koji Morita, Kariya (JP)

(73) Assignees: Francois Pierrot, Saint-Jean-de-Vedas (FR); Olivier Company, Gignac (FR); Toyoda Koki Kabushiki Kaisha, Kariya (JP)

( * ) Notice: Subject to any disclaimer, the term of this patent is extended or adjusted under 35 U.S.C. 154(b) by 0 days.

(21) Appl. No.: 09/662,743

(22) Filed: Sep. 15, 2000

(30) Foreign Application Priority Data

Sep. 17, 1999 (JP) .......................................... 11-264311

(51) Int. Cl.$^7$ ................................................. B25J 9/06
(52) U.S. Cl. ................................ 74/490.01; 74/490.03; 901/16; 901/23
(58) Field of Search ................... 74/479.01, 490.01, 74/490.03, 490.05, 490.07, 490.08; 414/729, 735; 901/23; 434/55, 58

(56) References Cited

U.S. PATENT DOCUMENTS

| | | | |
|---|---|---|---|
| 4,732,525 A | | 3/1988 | Neumann |
| 4,801,239 A | | 1/1989 | Austad |
| 4,976,582 A | | 12/1990 | Clavel |
| 5,259,710 A | | 11/1993 | Charles |
| 5,333,514 A | | 8/1994 | Toyama et al. |
| 5,746,138 A | | 5/1998 | Hirose |
| 6,038,940 A | * | 3/2000 | Rosheim ...................... 434/55 |
| 6,047,610 A | * | 4/2000 | Stocco et al. ............. 74/479.01 |
| 6,105,455 A | * | 8/2000 | Rosheim .................. 74/490.03 |

FOREIGN PATENT DOCUMENTS

| | | |
|---|---|---|
| FR | 2 672 836 | 8/1992 |
| JP | 2-284842 | 11/1990 |
| JP | 3-111182 | 5/1991 |
| JP | 3-294193 | 12/1991 |
| JP | 7-116983 | 5/1995 |
| JP | 9-066480 | 3/1997 |

OTHER PUBLICATIONS

Francois Pierrot, Proceedings of the 1999 IEEE/ASME International Conference on Advanced Intelligent Mechatronics, pp. 508–513, "H4: A New Family of 4–DOF Parallel Robots", Sep. 19–23, 1999.

Luc Rolland, Proceedings of the ASME, Dynamic Systems and Control Division—Conference IMECE '99, pp. 831–844, "A Novel 4–DOF Parallel Mechanism for Industrial Handling", Nov. 10–14, 1999 (retrieved copy from the Internet, pp. 1–9).

* cited by examiner

Primary Examiner—William C Joyce
(74) Attorney, Agent, or Firm—Oblon, Spivak, McClelland, Maier & Neustadt, P.C.

(57) ABSTRACT

A four-degree-of-freedom parallel robot capable of displacing a traveling plate with four degrees of freedom at a high speed and a high acceleration and positioning the traveling plate with high rigidity and high precision. The four-degree-of-freedom parallel robot has four actuators fixed to a base, four parallel linkages each of which is coupled at its upper end to a tip end of an arm of each of the actuators through a kinematic element such as a universal joint, and a traveling plate whose four corners are coupled to lower ends of the parallel linkages through kinematic elements. By controlling the actuators, a main member of the traveling plate is displaced with four degrees of freedom, i.e., translated in all directions and rotated around a predetermined axis. Only axial forces are applied to rods constituting the parallel linkages. Thus, the traveling plate can be positioned at a high speed and with high rigidity as well as high precision.

6 Claims, 14 Drawing Sheets

FOUR-DEGREE-OF-FREEDOM PARALLEL ROBOT

INCORPORATION BY REFERENCE

The disclosure of Japanese Patent Application No. HEI 11-264311 filed on Sep. 17, 1999 including the specification, drawings and abstract is incorporated herein by reference in its entirety.

BACKGROUND OF THE INVENTION

1. Field of the Invention

The present invention relates to a technical field of a parallel robot wherein a plurality of actuators are disposed in parallel. Although the present invention is suited for an industrial robot designed for transportation, processing or machining, it is also widely applicable to other devices such as a driving simulator for a motor vehicle.

2. Description of the Related Art

The industrial robot is classified into a serial robot such as an arm-type robot with a serial linkage mechanism wherein actuators are disposed in series and a parallel robot such as a flight simulator with a parallel linkage mechanism wherein actuators are disposed in parallel. In the parallel robot, unlike the case with the serial robot, there is no bending moment applied to rods constituting the linkage mechanism. That is, only a tensile or compressive axial force is applied to the rods. Thus, the parallel robot is capable of operating at a high speed and a high acceleration and ensuring high rigidity.

Parallel robots having six degrees of freedom (related art I), such as a flight simulator, are disclosed in U.S. Pat. No. 5,333,514 and U.S. Pat. No. 5,175,729 and have already been commercialized. In these six-degree-of-freedom parallel robots, a traveling plate can be translated in all directions along three orthogonal axes and rotated around the three orthogonal axes. In other words, the traveling plate can operate with an extremely high degree of freedom. However, six actuators are required to realize movements with six degrees of freedom in such a six-degree-of-freedom parallel robot. It is impossible to dispense with these actuators. Therefore, there is inevitably a limit imposed on an attempt to cut down the cost. This limit makes the six-degree-of-freedom parallel robot expensive.

It is considered that flight simulators for simulating maneuver of an aircraft need to have six degrees of freedom. However, industrial robots do not always require six degrees of freedom. That is, many industrial robots operate satisfactorily as long as they can be displaced with four degrees of freedom, i.e., can be translated in longitudinal, lateral and vertical directions and rotated in a horizontal plane. A specification with six degrees of freedom is an overburden for industrial robots.

Thus, U.S. Pat. No. 4,976,582 discloses a pseudo-parallel robot capable of moving with the aforementioned four degrees of freedom. This robot will be referred to as "related art II" to be distinguished from a four-degree-of-freedom parallel robot of the present invention.

The robot of the related art II has three parallel linkages each of which has two rods driven by an actuator. These parallel linkages make it possible to translate a traveling plate with three degrees of freedom. To enable the traveling plate to be turned in a horizontal plane, the robot of the related art II has a freely expandable torque rod which is rotationally driven by a fourth actuator. The torque rod is coupled at one end to a shaft of a rotational motor through a universal joint and at the other end to a central portion of the traveling plate through a universal joint. Therefore, the traveling plate follows rotational movement of the drive shaft of the rotational motor and is rotated in the horizontal plane.

In the robot of the related art II, the number of actuators can be reduced to four. As a result, this robot is less expensive than the aforementioned six-degree-of-freedom parallel robot which requires six actuators.

However, in the robot of the related art II, since a torsional moment is applied to the torque rod, it is difficult to accomplish a movement at a high speed and a high acceleration as intrinsically required of the parallel robot. That is, if a great torque is applied to the torque rod, it undergoes torsional information. For this reason, the robot of the related art II cannot be rotated as precisely as those of the related art I. If the robot of the related art II is stopped from being rotated all of a sudden, it causes torsional vibrations. In this case, it takes a long time to position the robot.

In addition, as described above, since the robot of the related art II has the torque rod susceptible to torsional deformation, its rigidity tends to be insufficient. Therefore, if a yawing moment is applied to the traveling plate, it is rotated in accordance with torsional deformation of the torque rod. As a result, the robot of the related art II is disadvantageous in that the traveling plate cannot easily be positioned with high rigidity and high precision.

SUMMARY OF THE INVENTION

It is thus an object of the present invention to provide a four-degree-of-freedom parallel robot capable of displacing a traveling plate with four degrees of freedom at a high speed and a high acceleration and positioning the traveling plate with high rigidity and high precision.

According to a first aspect of the present invention, a four-degree-of-freedom parallel robot comprising a base, four actuator fixed to said base, four rod members each of which is coupled at one end to a movable portion of said actuators through a kinematic element, and a traveling plate whose four corners are coupled to the other ends of said rod members through kinematic elements, wherein at least part of said traveling plate can be displaced with four degrees of freedom which are defined by linear motions along three orthogonal axes and one rotation around a predetermined axis.

In the first aspect of the present invention, the four actuators are controlled in an interconnected manner. If the four rod members are pushed or pulled by predetermined strokes, the traveling plate is displaced by the rod members. The main portion of the traveling plate moves with a limited number of degrees of freedom, i.e., four degrees of freedom. That is, the main portion can be translated in all directions and rotated around a predetermined axis. Therefore, if a position of one end of each of the four rod members on the side of the actuators is determined, a position of the other end of each of the rod members on the side of the traveling plate is also determined. Thus, the position and posture of the traveling plate is determined uniquely.

That is, if strokes of the four actuators are determined, the main portion of the traveling plate is positioned at one point in a three-dimensional space through the four rod members. Also, the posture of the traveling plate is determined by a predetermined rotational position around a predetermined axis. In this process, only a tensile or compressive axial force is applied to each of the rod members. That is, these rod members are free of moment as to torsional deformation.

Therefore, if it is ensured that there is no clearance in kinematic elements and the like for the rod members, the traveling plate is fixed to a predetermined position in the three-dimensional space in a predetermined posture with high rigidity as well as high precision. Further, when the actuators are driven to displace the traveling plate, only an axial force is applied to each of the rod members. That is, the rod members have extremely high rigidity and are thus able to endure a great inertia force. Thus, the traveling plate can be accelerated or decelerated at a high acceleration within the range of driving forces of the actuators. As a result, it becomes possible to perform high-speed operation within the range of driving speeds of the actuators.

Thus, the four-degree-of-freedom parallel robot in accordance with the first aspect of the present invention has the effect of displacing the main portion of the traveling plate with four degrees of freedom at a high speed and a high acceleration and positioning the main portion with high rigidity and high precision. This effect cannot be achieved by the aforementioned robot of the related art II.

In addition, the number of actuators can be reduced in comparison with the aforementioned six-degree-of-freedom parallel robot. Therefore, the parallel robot in accordance with the first aspect of the present invention can be manufactured at a lower cost than the six-degree-of-freedom parallel robot.

According to a second aspect of the present invention, a four-degree-of-freedom parallel robot comprising a base, four actuator rods each of which is fixed at one end to said base through a kinematic element and which can be expanded or contracted to desired length, a traveling plate whose four corners are coupled to the other ends of said actuator rods through kinematic elements, wherein at least part of said traveling plate can be displaced with four degrees of freedom, which are linear motions along three orthogonal axes and one rotation around a predetermined axis.

The second aspect of the present invention achieves substantially the same effect as of the aforementioned first aspect. In addition, there is no actuator fixed to the base, and the actuator rods which serve as the actuators and the rod members of the first aspect are adopted. Thus, the overall structure is simplified, and a reduction in size and weight is made possible. For a similar reason, it also becomes possible to further cut down the cost.

Thus, in addition to the effect of the aforementioned first aspect, the second aspect of the present invention achieves the effect of making further reductions in size, weight and cost possible.

BRIEF DESCRIPTION OF THE DRAWINGS

The foregoing and further objects, features and advantages of the present invention will become apparent from the following description of preferred embodiments with reference to the accompanying drawings, wherein.

DETAILED DESCRIPTION OF PREFERRED EMBODIMENTS

Hereinafter, embodiments of a four-degree-of-freedom parallel robot of the present invention will be described clearly and sufficiently so that those skilled in the art can implement the present invention.

1. Embodiment I (Construction of Embodiment I)

Figure 1:
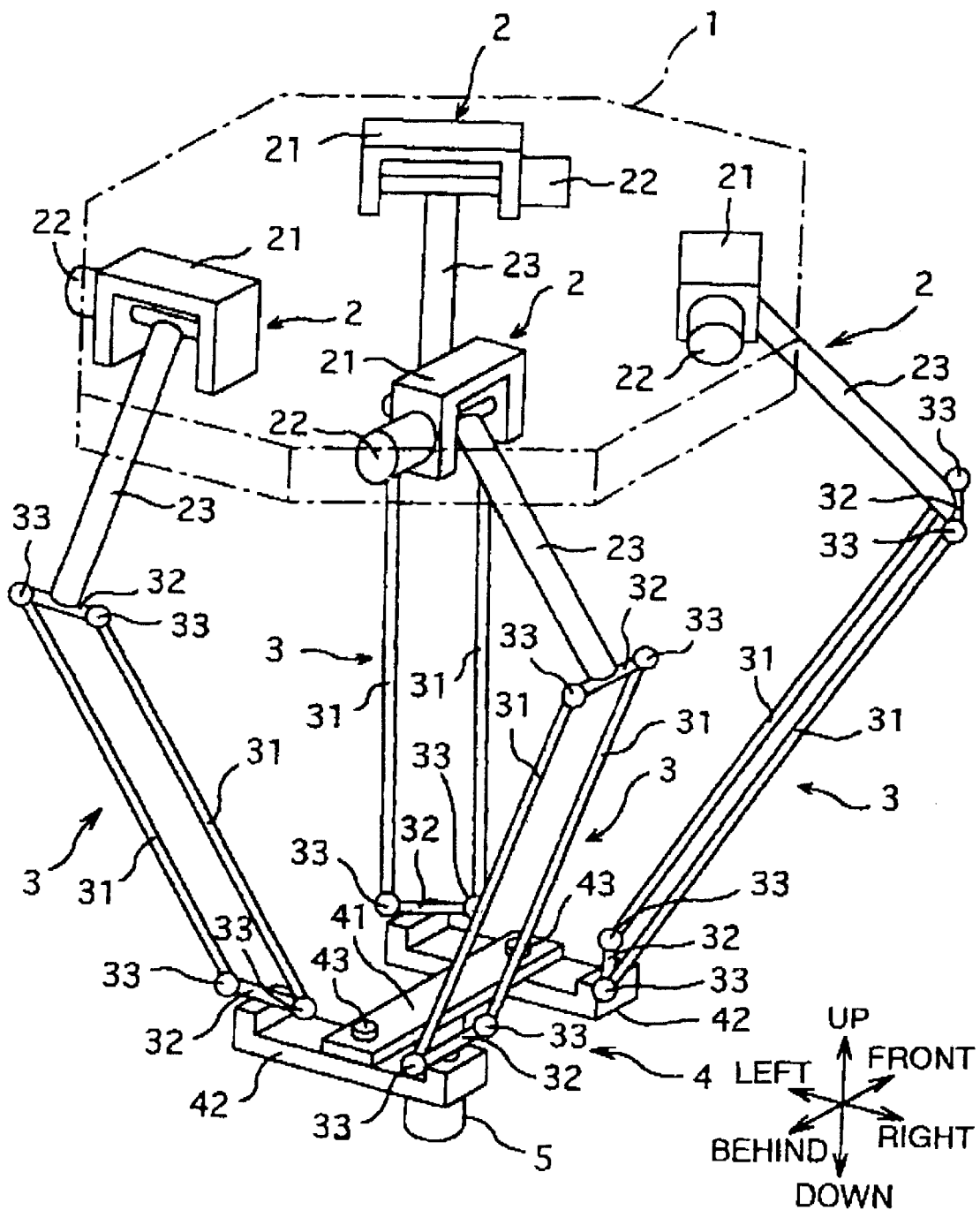
FIG. 1 is a perspective view of the structure of a four-degree-of-freedom parallel robot in accordance with a first embodiment of the present invention.

As shown in FIG. 1, a four-degree-of-freedom parallel robot in accordance with a first embodiment of the present invention has a base 1, four actuators 2 and rod members (parallel linkage 3), a traveling plate 4, and an end effector 5.

The base 1 is made of a rigid metal plate which is in the shape of an equilateral octagon as viewed in a plan view. The base 1 is disposed horizontally and fixed on its upper surface to a frame (not shown). Brackets 21 of the four actuators 2 are respectively fixed to four corners of a lower surface of the base 1 at predetermined positions and predetermined angles.

Each of the four actuators 2 fixed to the base 1 is composed of the bracket 21, a rotational motor 22 fixed to the bracket 21, and an arm 23 which is fixed at one end to a drive shaft rotationally driven by the rotational motor 22 within a predetermined angular range. The rotational motors 22 are servo-motors which are controlled independently by later-described control means.

Each of the four rod members is coupled at one end to a tip end of the arm 23 serving as a movable portion of the actuator 2 through a kinematic element such as a universal joint 33. To be more specific, each of the rod members is constructed of two long rods 31 which are parallel to each other. The long rods 31, a pair of short end members 32 which are parallel to each other, and four universal joints 33 which rotatably couple the rods 31 to the end members 32 constitute a parallel linkage 3. End members 32 constituting opposed end portions of each parallel linkage 3 are coupled to the actuator 2 and the traveling plate 4.

That is, each parallel linkage 3 is composed of two rods 31, a pair of end members 32, and universal joints 33 which rotatably couple the rods 31 and the end members 31, and is always in the shape of a parallelogram. One of the end members 32 of each parallel linkage 3 is coupled to a tip end of the arm 23 of the actuator 2, and the other is coupled to an end of a coupling member 42 of the traveling plate 4.

The end member 32 fixed to the tip end of the arm 23 of the actuator 2 is fixed in parallel to a drive shaft of the actuator 2. Thus, the drive shaft of each actuator 2 is kept parallel to the end members 32 at opposed ends of a corresponding one of the parallel linkages 3.

The traveling plate 4 is coupled at four corners to the end members 32 at lower ends of the respective parallel linkage 3 through universal joints 33. The traveling plate 4 has a main member 41 whose lower portion is fixed to the end effector 5 and a pair of coupling members 42 whose intermediate portions are relatively rotatably coupled to opposed ends of the main member 41 and whose opposed end portions are coupled to the end members 32 of the parallel linkage 3. That is, the traveling plate 4 is composed of the main member 41, a pair of the coupling members 42, and a pair of pivots 43 which connect the intermediate portions of the coupling members 42 to the opposed ends of the main member 41 such that the main member can rotate relative to each coupling members around a vertical axis.

Figure 2:
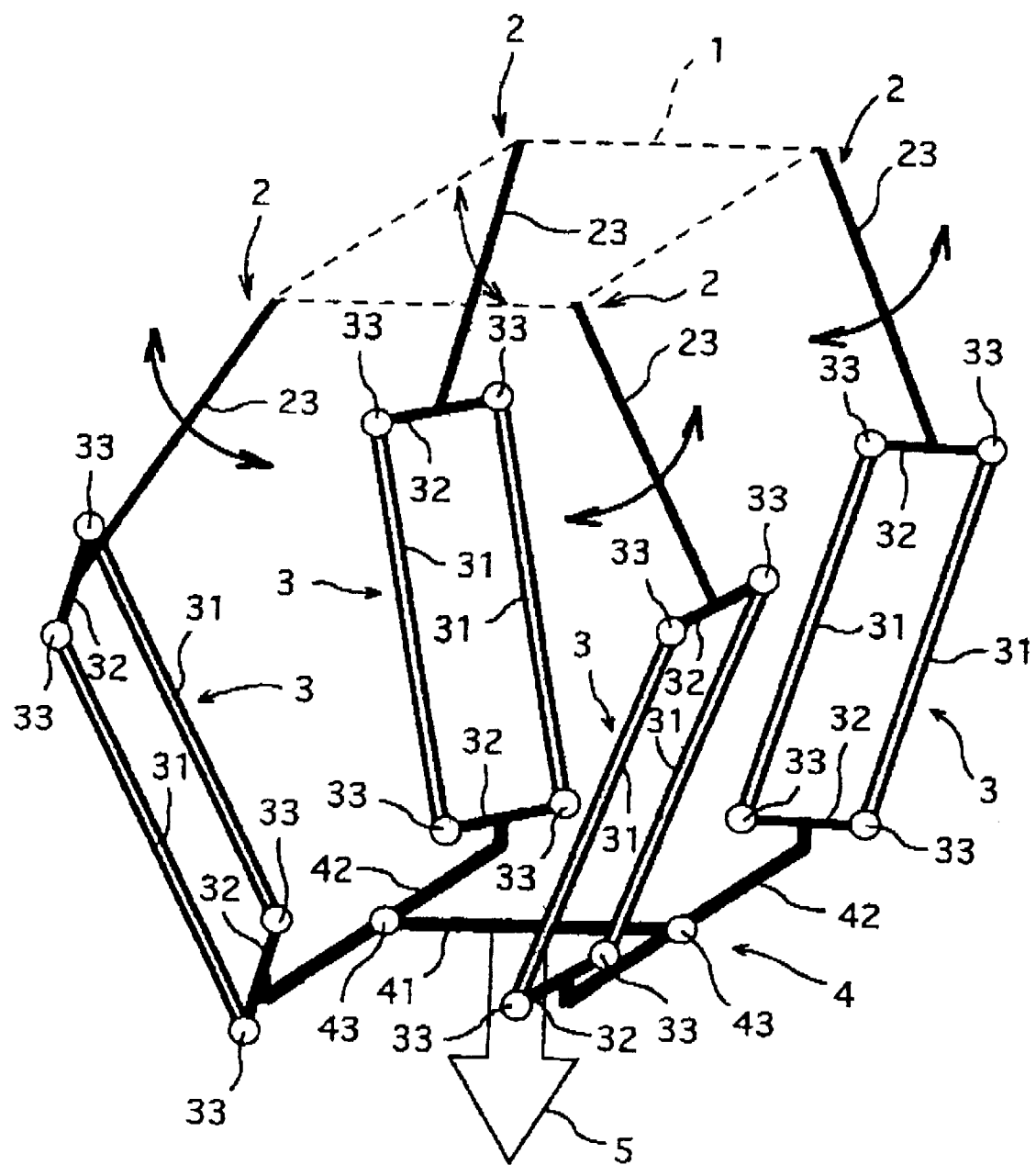
FIG. 2 is a schematic perspective view of the structure of a linkage mechanism in accordance with the first embodiment of the present invention.

By suitably controlling the actuators 2, the main member 41 of the traveling plate 4 is capable of moving with four degrees of freedom. That is, the main member 41 can be translated in all directions, i.e., longitudinally, laterally and vertically, and rotated around the vertical axis. That is, as shown in FIG. 2, the arms 23 of the actuator 2, the parallel linkage 3, and the traveling plate 4 constitute a linkage mechanism. Therefore, as described above, the main member 41 of the traveling plate 4 can change its position and posture with four degrees of freedom. In FIG. 2, sixteen universal joints 33 and a pair of pivots 43 are denoted by small circles.

Figure 3:
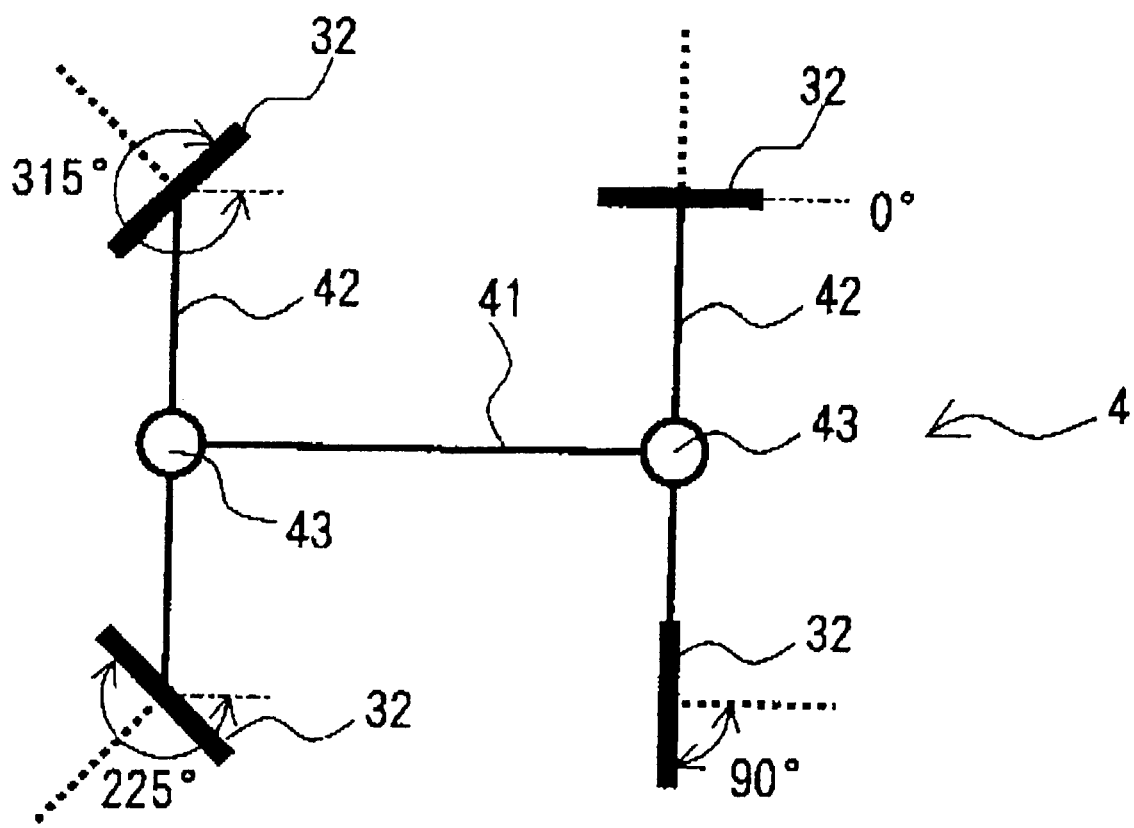
FIG. 3 is plan view of mounting directions of rod members in accordance with the first embodiment of the present invention.
Figure 3:
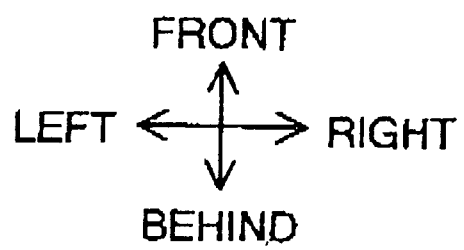

FIG. 3 shows a combination of directions of the end members 32 of the parallel linkages 3 which are coupled to the four corners of the traveling plate 4. Four end members 32 of the parallel linkages 3 are fixed to one pair of end members 32 of the traveling plate 4 in the following manner. That is, assuming the direction of the right-front end member 32 as a reference direction, the end members 32 are sequentially rotated clockwise by angles of 0°, 90°, 225° and 315°. Such a combination of mounting directions of the end members 32 is determined such that the traveling plate 4 is located directly under the center of the base 1 and that the coupling members 42 are perpendicular to the main member 41.

Such a combination of mounting angles of the end members 32 is determined such that static indetermination is prevented from being caused through generation of a singular point (a stationary singular point and a uncertain singular point) in motion of the linkages. Besides, such a combination of mounting angles of the end members 32 is determined such that the main member 41 of the traveling plate 4 becomes sufficiently stable in position and posture.

Referring again to FIG. 1, the end effector 5 is fixed to the main member 41 of the traveling plate 4 and protrudes downwards. The end effector 5 can be exchanged in accordance with use of the four-degree-of-freedom parallel robot of the embodiment. A control signal and power are supplied to the end effector 5 through a signal line (not shown) and a power line (not shown) respectively. The signal line and the power line may be suspended from the base while being suitably supported thereby. Alternatively, the signal line and the power line may be disposed along one of the arms 23 and one of the parallel linkages 3.

The end effector 5 may be a handling device for transferring works and supporting the works at predetermined positions or a main-spindle device of a machine tool for machining workpices.

Figure 4:
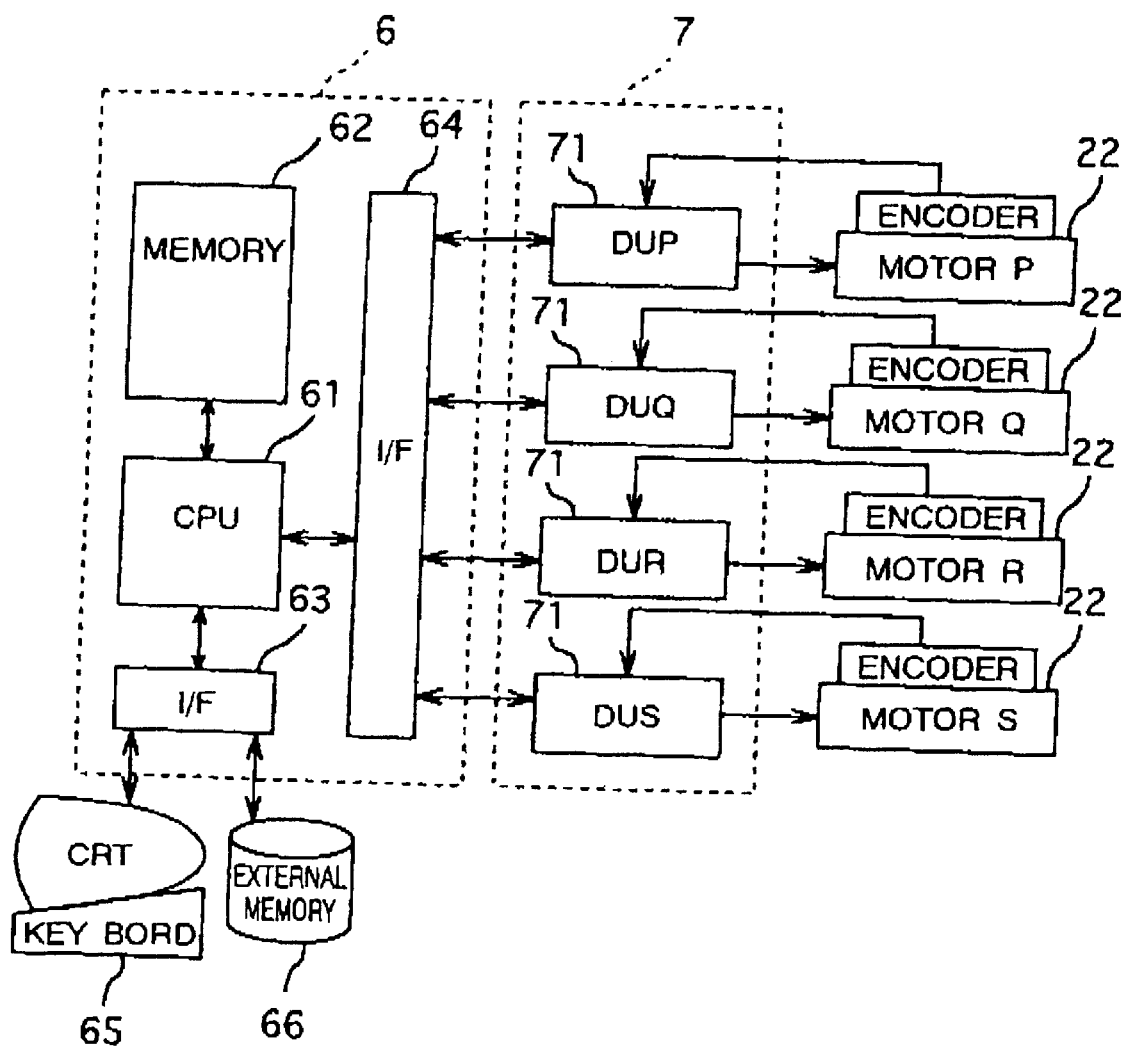
FIG. 4 is a flowchart of the essential part of a control logic in accordance with the first embodiment of the present invention.

As shown in FIG. 4, the control means is composed of a control device 6 which is a digital computer and a drive circuit 7 which is attached to the control device 6. The control device 6 is composed of a CPU 61, a memory 62, interfaces 63, 64 and the like. The control device 6 is connected to an I/O device 65 and an external memory 66 through the interface 63. The I/O device 65 is a man-machine interface composed of a key board and a CRT display. The external memory 66 is a hard disk. A control program for controlling the four-degree-of-freedom parallel robot of the embodiment according to a predetermined sequence is stored in the external memory 66. Thus, the four-degree-of-freedom parallel robot of the embodiment can carry out various works through replacement of the control program.

A coordinate-conversion program for calculating rotational angular positions to be assumed by the rotational motors 22 based on command values for a position and a posture to be assumed by the main member 41 of the traveling plate 4 is stored in the memory 62 of the control device 6. The position and the posture to be assumed by the main member 41 are designated by the external memory 66.

Figure 5:
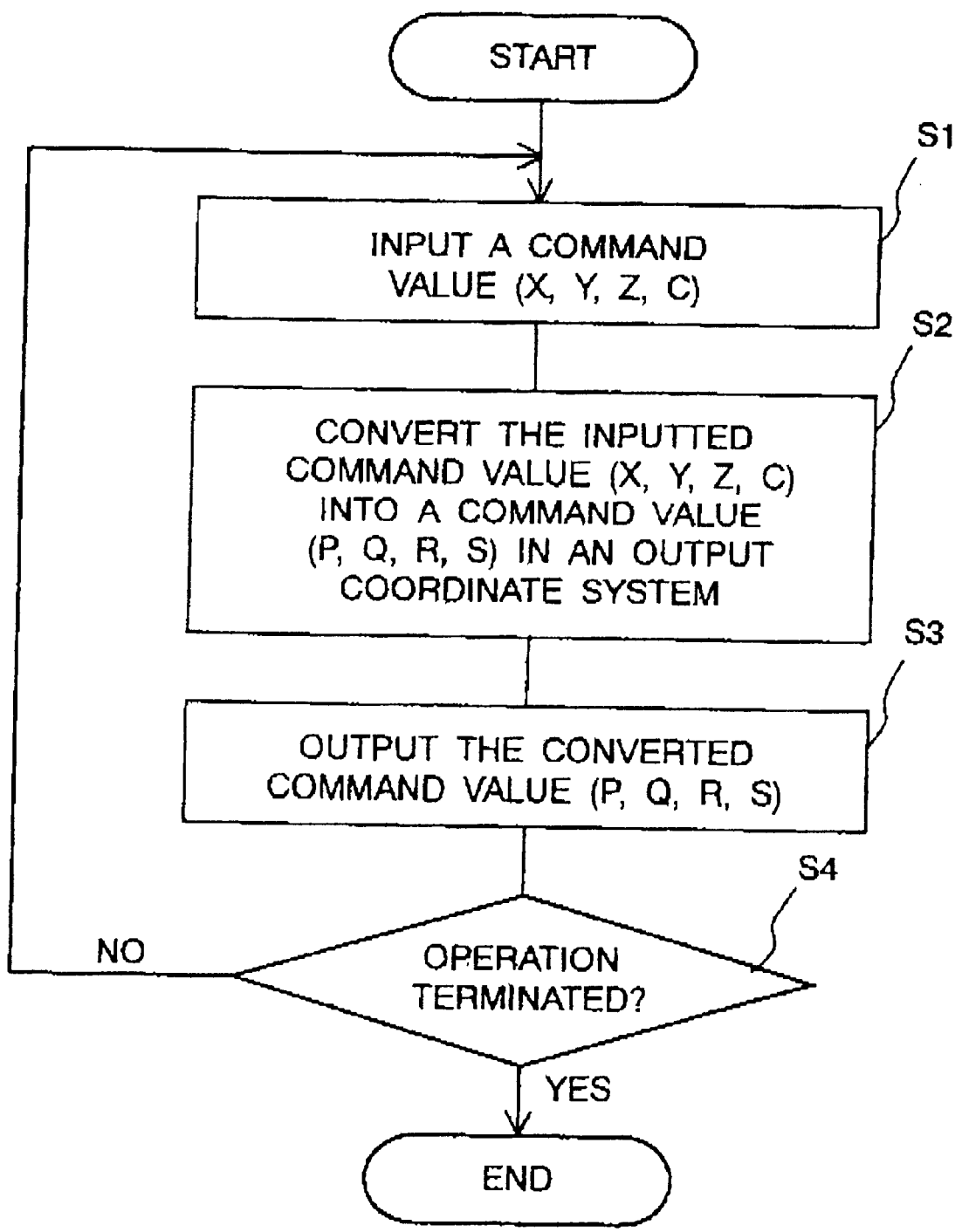
FIG. 5 is a block diagram of the structure of a control device in accordance with the first embodiment of the present invention.

As shown in FIG. 5, this coordinate-conversation program is a program wherein an input command value is read in a processing step S1, wherein coordinate conversion is carried out in a processing step S2, and wherein a command value after the coordinate conversion is outputted in a processing step S3. These processings are repeated until it is judged in a judgment step S4 that the operation has been terminated.

The input command value (X, Y, Z, C) is composed of four values designative of longitudinal, lateral and vertical positions (X, Y, Z) and yawing posture C to be assumed by the main member 41 of the traveling plate 4. On the other hand, the command value after the coordinate conversion, i.e., the output coordinate system (P, Q, R, S) is composed of rotational angular positions to be assumed by the four rotational motors 22 respectively. During coordinate conversion in the processing step S2, linear computation is carried out to solve quaternary simultaneous equations.

Referring again to FIG. 4, if command values (P, Q, R, S) for the respective rotational motors 22 are calculated, the command values are supplied to four drive units 71 of the drive circuit 7 through the interface 64. Then, each of the drive units 71 smoothly drives a corresponding one of the rotational motors 22 and sets its rotational angular position as indicated by the command value.

Encoders for detecting rotational angular positions with a high resolution are attached to the rotational motors 22, and a feedback loop is formed between the drive units 71 and the rotational motors 22. Therefore, rotational angular positions of the rotational motors 22 are controlled with sufficient precision.

(Operation and Effect of Embodiment I)

Because the four-degree-of-freedom parallel robot of this embodiment is constructed as described above, it can mainly achieve the following two operations and effects.

As for the first effect, the main member 41 of the traveling plate 4 can be displaced with four degrees of freedom at a high speed and a high acceleration, and positioned with high rigidity as well as high precision.

That is, in the four-degree-of-freedom parallel robot of this embodiment, the four actuators 22 are controlled in an interconnected manner, so that the four parallel linkages 3 are pushed or pulled by their predetermined strokes respectively. Then, the traveling plate 4 is displaced by the parallel linkages 3, whereby positions and postures of the main member 41 of the traveling plate 4 and a pair of the coupling members 42 are determined.

The main member 41 of the traveling plate 4 has a limited number of degrees of freedom, i.e., four degrees of freedom. That is, the main member 41 can be translated in all the directions and rotated around a predetermined axis. Thus, in the four parallel linkages 3, if positions of the end members 32 on the side of the actuator 2 are determined, positions of the end members 32 on the side of the traveling plate 4 are also determined uniquely. As a result, positions and postures to be assumed by the main member 41 of the traveling plate 4 and a pair of the coupling members 42 are determined uniquely.

In other words, if strokes of the four actuators 2 are determined, the position of the main member 41 of the traveling plate 4 is determined through the four parallel linkages 3 at a point in a three-dimensional space. Besides, the posture of the main member 41 of the traveling plate 4 is also determined at a predetermined rotational position around the vertical axis. In this case, only a tensile or compressive axial force is applied to the rods 31 of the parallel linkages 3. The rods 31 are free of moment as to torsional deformation.

Therefore, it is preferable that the actuator 2 operate with sufficient precision, that the universal joints 33 at opposed ends of the rods 32 be free from clearance, and that the arm 23, the parallel linkages 3 and the traveling plate 4 be sufficiently rigid. If these conditions are satisfied, the main member 41 of the traveling plate 4 is fixed to the designated position in the designated posture in the three-dimensional space with high rigidity as well as high precision.

Further, when the traveling plate 4 is displaced by moving the respective actuators 2, the rods 31 of the parallel linkages 3 have extremely high rigidity because only an axial force is applied thereto. Thus, the parallel linkages 3 are able to endure a great inertia force. Therefore, the traveling plate 4 can be accelerated and decelerated at a high acceleration within the range of driving forces of the actuators 2. As a result, it is also possible to perform high-speed operation within the range of driving speeds of the actuators 2.

Thus, the four-degree-of-freedom parallel robot of this embodiment has the effect of displacing the main member 41 of the traveling plate 4 with four degrees of freedom at a high speed and a high acceleration, and positioning the main member 41 with high rigidity as well as high precision. This effect cannot be achieved by the aforementioned related art II.

Besides, in the four-degree-of-freedom parallel robot of this embodiment, the number of actuators 2 can be reduced in comparison with the aforementioned six-degree-of-freedom parallel robot. Thus, the four-degree-of-freedom parallel robot of this embodiment also has the effect of being manufactured at a lower cost in comparison with the six-degree-of-freedom parallel robot.

As for the second effect, structural design and the manufacture of software can be carried out more easily. Thus, in addition to the aforementioned reduction in number of actuators 2, the cost can further be reduced.

That is, in the four-degree-of-freedom parallel robot of this embodiment, all the four rod members 3 are designed as the parallel linkages 3 each of which has two parallel rods 31. The parallel linkages 3 are of the same standard. As a result, the four parallel linkages 3 can be manufactured according to the same standard. This makes it possible to reduce the number of different parts, carry out structural design and the manufacture of software easily, and cut down the cost. This effect of cutting down the cost is remarkable especially in the case of small-scale production.

In this embodiment, as described above, the end members 32 of the parallel linkages 3 are fixed to the coupling members 42 of the traveling plate 4 at predetermined angles. That is, the end members 32 of the parallel linkages 3 and the drive shafts of the actuators 2 are mounted to the four corners of the traveling plate 4 with angular differences of integral multiplies of 45°. Furthermore, two pairs of the end members 32 are mounted with an angular difference of 90°.

Thus, predetermined coordinate conversion is performed based on a target position and a target posture to be assumed by the main member 41 of the traveling plate 4 in the three-dimensional space, and the processing algorithm for calculating target strokes of the four actuators 2 is simplified. As a result, it becomes easy to develop a control program for the control device 6 for controlling the four actuators 2. Further, since the processing algorithm for coordinate conversion is simplified as described above, the control processing proceeds smoothly for the processing performance of the control device 6. Thus, it becomes possible to smoothly displace the traveling plate 4 to its target position.

Thus, the four-degree-of-freedom parallel robot of this embodiment has the effect of facilitating structural design and the manufacture of control software and cutting down the cost. In addition, even though the control device 6 is inexpensive, relatively smooth operation is accomplished.

(Modification Example I of Embodiment I)

As a modification example I of this embodiment, it is possible to realize a four-degree-of-freedom parallel robot which is different from the embodiment I in combination of mounting angles of the actuators 2 and the parallel linkages 3 to the base 1 and the traveling plate 4.

In this modification example, directions of the parallel linkages 3 are coupled to the four corners of the traveling plate 4 can be combined as will be described below. That is, assuming a predetermined direction as a reference direction around the vertical axis which is an axis of rotational motion, the following combinations are possible in one rotational direction. In this case, the mounting angles of the parallel linkages 3 are mounting angles of the end members 32 at lower ends of the four parallel linkages 3 with respect to the traveling plate 4. It is recommended to refer to these mounting angles in conjunction with FIG. 3.

Figure 6:
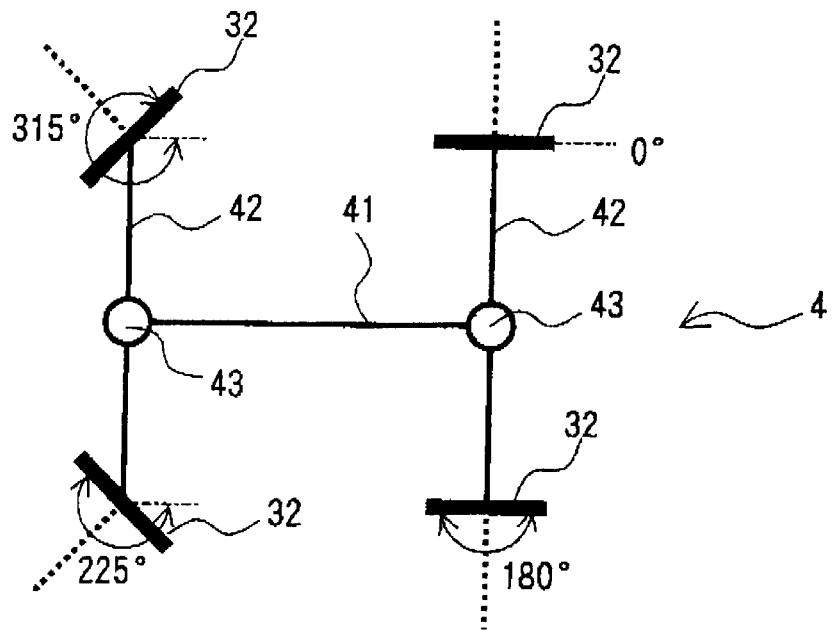
FIG. 6 is a plan view of mounting directions of rod members in accordance with a first modification example of the first embodiment of the present invention.
Figure 7:
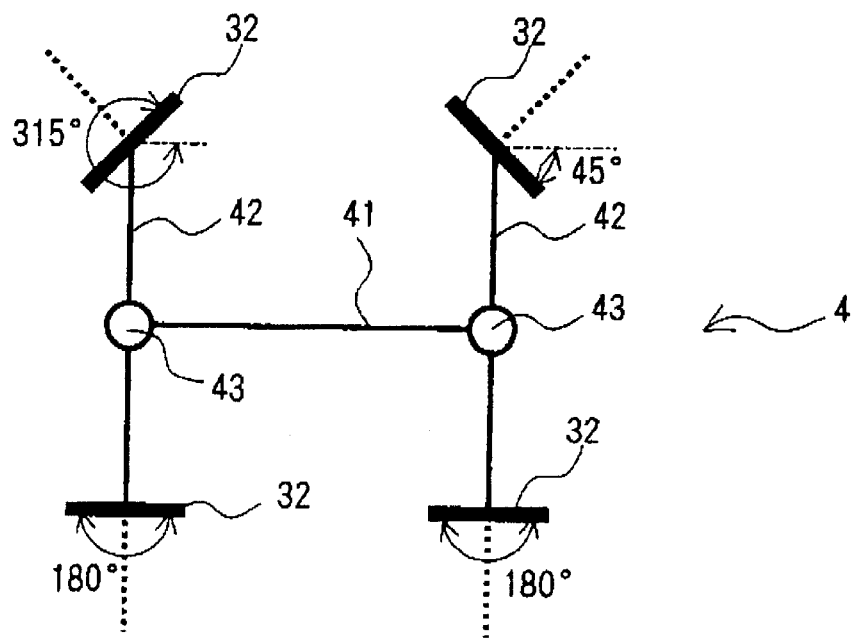
FIG. 7 is a plan view of mounting directions of the rod members in accordance with the first modification example of the first embodiment of the present invention.
Figure 8:
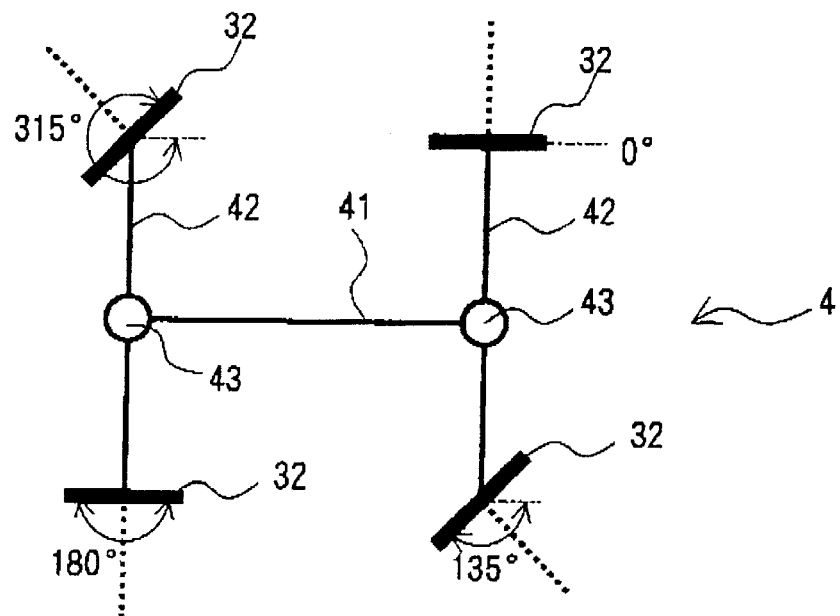
FIG. 8 is a plan view of mounting directions of the rod members in accordance with the first modification example of the first embodiment of the present invention.
Figure 9:
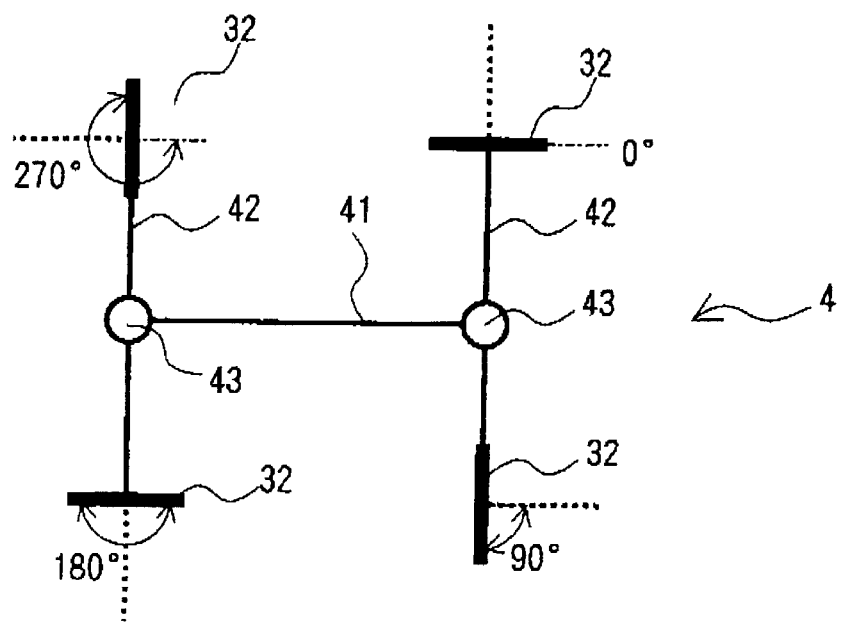
FIG. 9 is a plan view of mounting directions of the rod member in accordance with the first modification example of the first embodiment of the present invention.

That is, mounting angles of the parallel linkages 3 in this modification example are determined according to one of the following four combinations. Any one of these combinations are possible.

a combination of 0°, 180°, 225° and 315° (see FIG. 6)
a combination of 45°, 180°, 180° and 315° (see FIG. 7)
a combination of 0°, 135°, 180° and 315° (see FIG. 8)
a combination of 0°, 90°, 180° and 270° (see FIG. 9)

Among these combinations, the combination shown in FIG. 9 is recommendable because the processing algorithm for coordinate conversion is simplified. As a matter of course, it is possible to adopt mounting angles according to a combination other than the aforementioned combinations unless generation of a singular point causes static indetermination or a surplus degree of freedom.

In the embodiment I and the modification example I, the joints of the parallel linkages 3 are all constructed of the universal joints 33. However, it is also possible to implement a modification example wherein some or all of the universal joints 33 are replaced by ball joints as the kinematic elements.

(Modification Example II of Embodiment I)

Figure 10:
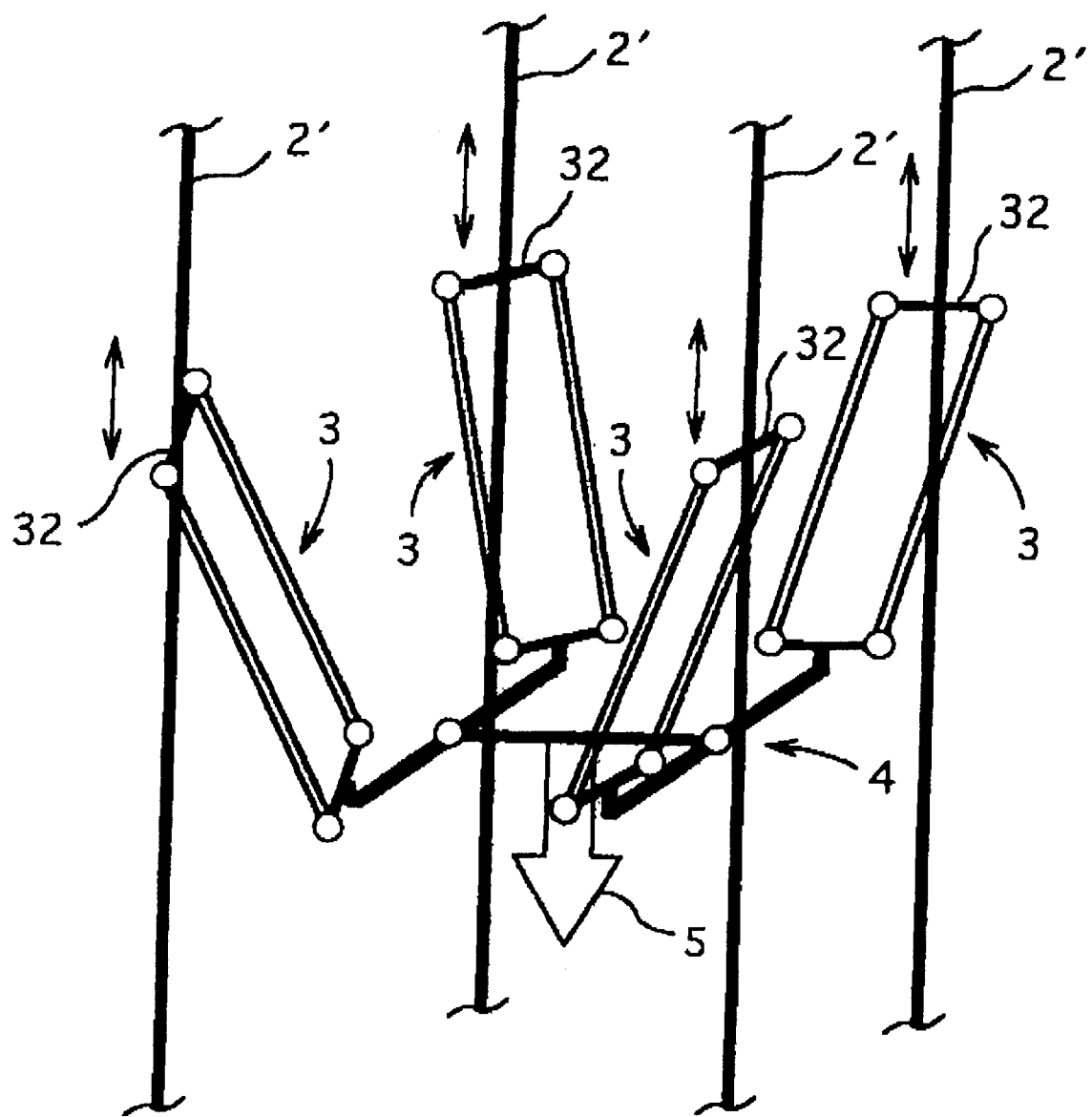
FIG. 10 is a schematic perspective view of the structure of a second modification example of the first embodiment of the present invention.

As a modification example II of this embodiment, as shown in FIG. 10, it is possible to realize a four-degree-of-freedom parallel robot which has four linear motors 2' as actuators in place of the four rotational motors 22 of the embodiment I. The linear motors 2' serving as actuators are secured to two bases (not shown). Rails of the linear motors 2' are secured at upper end portions to one of the bases, and at lower end portions to the other base.

Each of the linear motors 2' is composed of a vertically extending long rail which is alternately magnetized and a slider which moves along the rail and into which an electromagnetic coil is built. The end member 32 at the upper end of the parallel linkage 3 is fixed to each slider at a predetermined angle. The rails of the four linear motors 2' extend vertically and are disposed in parallel with one another.

Therefore, due to the operation of the linear motors 2', the end members 32 at the upper ends of the parallel linkages 3 are vertically displaced while being maintained at predetermined mounting angles. By suitably controlling amounts of displacement, it becomes possible to move the traveling plate 4 at a high speed with four degrees of freedom as is the case with the embodiment I and securely position the traveling plate 4. Thus, it is possible to achieve substantially the same effect as in the embodiment I.

In addition, the rails of the linear motors 2' are long and parallel to one another, and extend vertically. Thus, the traveling plate 4 can be displaced along the rails of the linear motors 2' as long as they exist. As a result, this modification example achieves the effect of significantly extending a moving range of the traveling plate 4 in the vertical direction.

Further, in this modification example, the end members 32 at the upper ends of the parallel linkages 3 remain at the same positions in the horizontal direction. Thus, the linkage mechanism of this modification example is simpler than that of the embodiment I. Therefore, the processing algorithm of coordinate conversion for calculating target positions of the linear motors 2' from a target position of the traveling plate 4 is further simplified. Thus, it is also possible to achieve the effect of reducing the calculating load of the control device 6.

Thus, this modification example not only achieves substantially the same effect as in the embodiment I but also achieves the effect of significantly extending the moving range of the traveling plate 4 in the vertical direction and reducing the calculating load of the control device 6.

(Modification Example III of Embodiment I)

Figure 11:
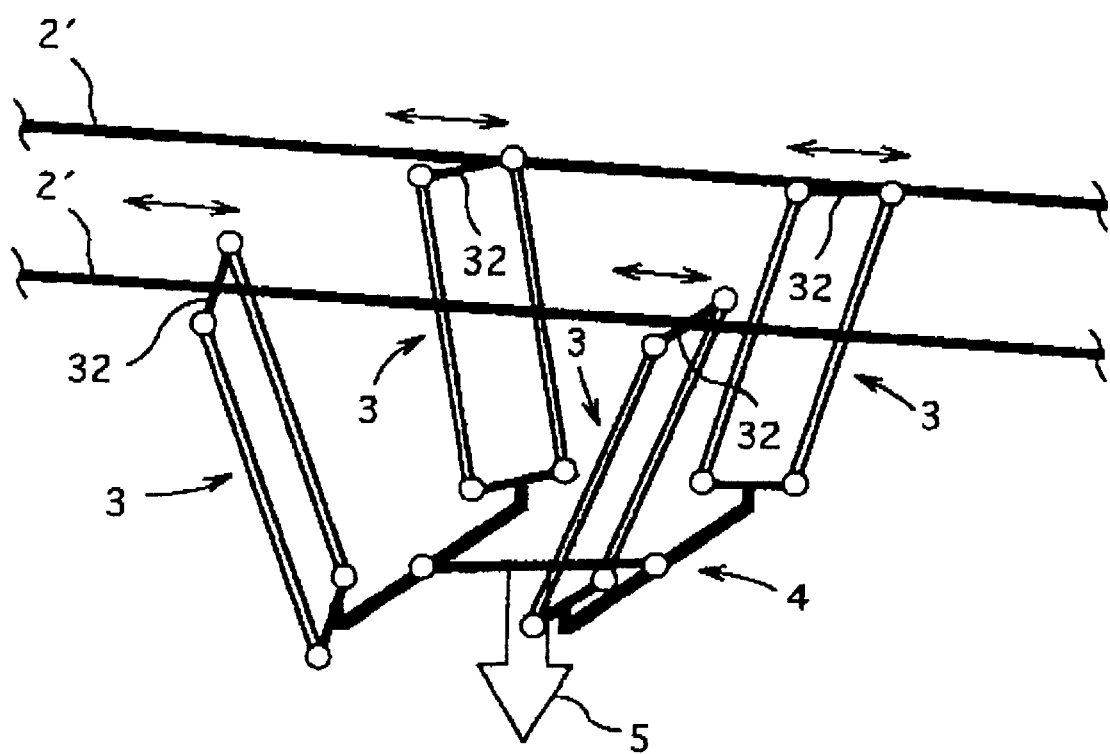
FIG. 11 is a schematic perspective view of the structure of a third modification example of the first embodiment of the present invention.

As a modification example III of this embodiment, as shown in FIG. 11, it is possible to realize a four-degree-of-freedom parallel robot which has two linear motors 2' as actuators in place of the four rotational motors 22 of the embodiment I. Unlike the aforementioned modification example II, this modification example employs two linear motors 2' whose rails are disposed horizontally in parallel with one another. Although not shown, two bases are provided to secure the linear motors 2' serving actuators. Rails of the linear motors 2' are secured at both ends to the bases.

Each of the linear motors 2' is composed of a horizontally extending long rail which is alternately magnetized and a pair of sliders which move along the rail and into which electromagnetic coils are built. The end members 32 at upper ends of the parallel linkages 3 are fixed to the sliders at predetermined angles. The two rails of the linear motors 2' extend horizontally and are disposed in parallel with each other.

Therefore, due to the operation of the linear motors 2', the end embers 32 at the upper ends of the parallel linkages 3 are horizontally displaced while being maintained at predetermined mounting angels. By suitably controlling amounts of displacement, it becomes possible to move the traveling plate 4 at a high speed with four degrees of freedom as is the case with the embodiment I and securely position the traveling plate 4. Thus, it is possible to achieve substantially the same effect as in the embodiment I.

In addition, the rails of the linear motors 2' are long and parallel to one another, and extend horizontally. Thus, the raveling plate 4 can be displaced along the rails of the linear motors 2' as long as they exist. As a result, this modification example achieves the effect of significantly extending a moving range of the traveling plate 4 in the horizontal direction.

Further, in this modification example, the end members 32 at the upper ends of the parallel linkages 3 remain at the same positions in the vertical direction. Thus, the linkage mechanism of this modification example is simpler than that of the embodiment I. Therefore, as is the case with the aforementioned modification example II, the processing algorithm of coordinate conversion for calculating target positions of the linear motors 2' from a target position of the traveling plate 4 is further simplified. Thus, it is also possible to achieve the effect of reducing the calculating load of the control device 6.

Thus, this modification example not only achieves substantially the same effect as in the embodiment I but also achieves the effect of significantly extending the moving range of the traveling plate 4 in the horizontal direction and reducing the calculating load of the control device 6.

(Modification Example IV of Embodiment I)

Figure 12:
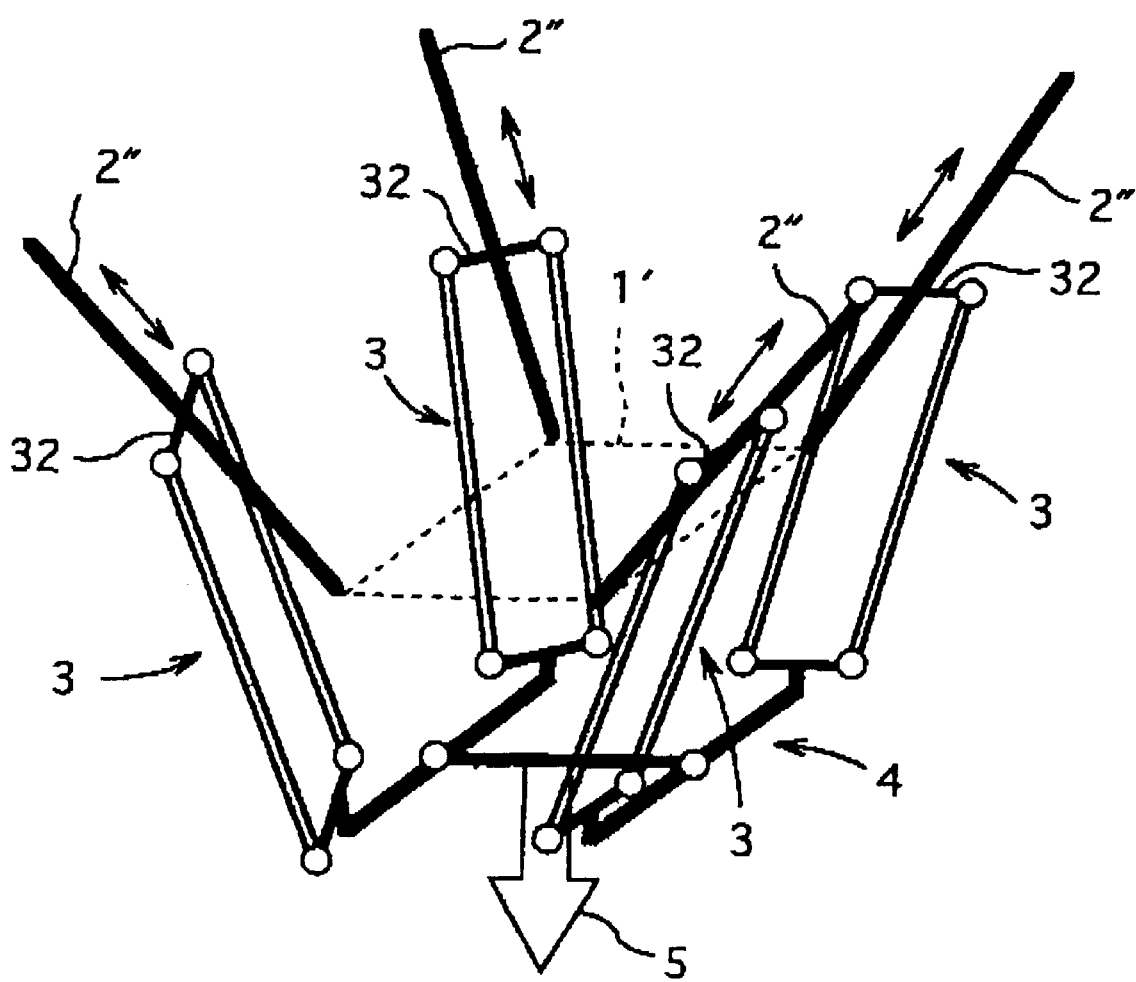
FIG. 12 is a schematic perspective view of the structure of a fourth modification example of the first embodiment of the present invention.

As a modification example IV of this embodiment, as shown in FIG. 12, it is possible to realize a four-degree-of-freedom parallel robot which has ball screw devices 2" as actuators in place of the rotational motors 22. The ball screw devices 2" are disclosed as "slide tables" in U.S. Pat. No. 5,715,729. It is thus recommended to refer to this publication in case of necessity.

In this modification example, the ball screw devices 2", which protrude upwardly and outwardly at predetermined angles from four corners of a generally square base 1', are fixed to the base 1'. The end members 32 at the upper ends of the parallel linkages 3 are fixed to nuts of the ball screw devices 2" at predetermined angles. Therefore, by suitably displacing the end members 32 of the parallel linkages 3 by means of the ball screw devices 2", it becomes possible to displace the traveling plate 4 with four degrees of freedom as is the case with the embodiment I. In addition, the ball screw devices 2" can be positioned with extremely high precision, have a great driving force, and are sufficiently rigid and almost free from clearance. Thus, the traveling plate 4 can be positioned with higher precision and higher rigidity.

Thus, the four-degree-of-freedom parallel robot of this modification example not only achieves substantially the same effect as in the embodiment I but also achieves the effect of positioning the traveling plate 4 with higher precision and higher rigidity.

(Modification Example V of Embodiment I)

Figure 13:
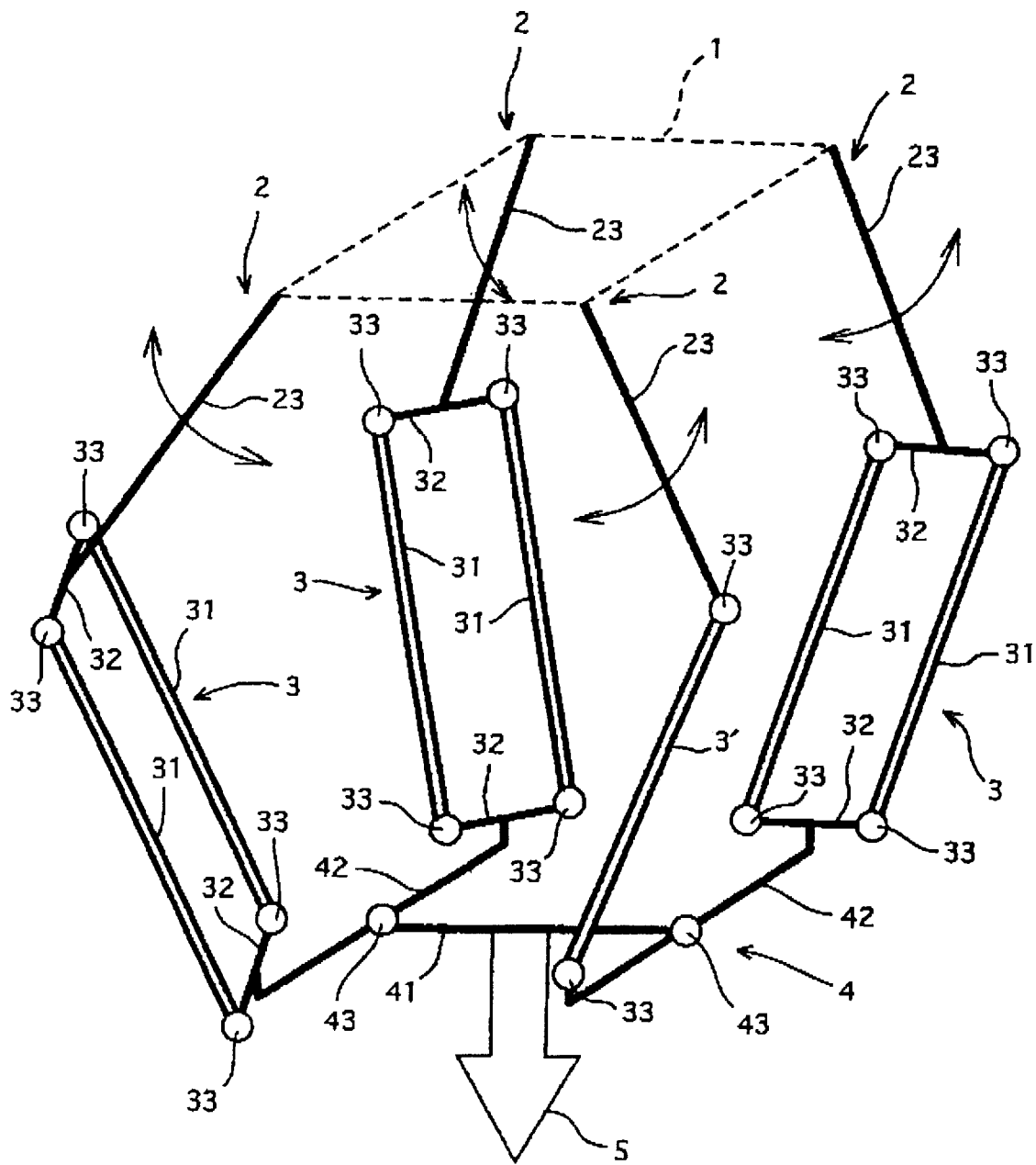
FIG. 13 is a schematic perspective view of the structure of a fifth modification example of the first embodiment of the present invention.

As the modification example V of this embodiment, as shown in FIG. 13, it is possible to realize a four-degree-of-freedom parallel robot which has at least one of unique rod 3' in place of parallel linkage 3. Then the unique rod 3' are coupled at both ends to the tip end of the arm 23 and the corner of the traveling plate 4 through universal joints 33. Since not ball joints but universal joints are coupled at both ends of the unique rod 3', it becomes possible to move the main member 41 of the traveling plate 4 with four degrees freedom as in the case with embodiment I. Thus, it is possible to achieve substantially the same effect as in the embodiment I.

(Modification Example VI of Embodiment I)

Figure 14:
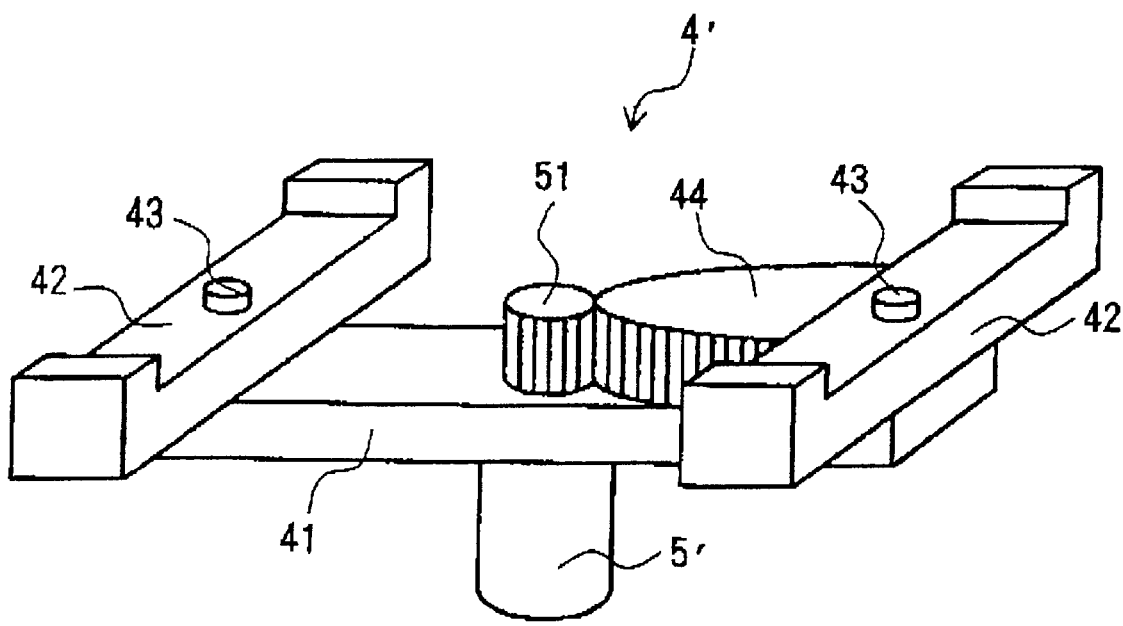
FIG. 14 is a perspective view of the structure of a traveling plate in accordance of the sixth modification example of the first embodiment of the present invention.

As a modification example VI of this embodiment, it is possible to realize a four-degree-of-freedom parallel robot which has another structure traveling plate 4' in place of the traveling plate 4. In FIG. 14, the traveling plate 4' has a main member 41, a pair of coupling member 42 whose intermediate portion are relatively rotatably coupled to opposed ends of main member 41, and a pair of pivots 43 which connect the intermediate portion of the coupling member 42 to the opposed ends of the main member 41 such that the main member can rotate relative to each coupling members around a vertical axis. The end effector 5' is attached intermediate portion of the main member 41. In the aforementioned embodiment I the end effector 5 is fixed to the main member 41, but in this modification example the end effector 5' is rotatably attached to the main member 41. And a first gear 51 is fixed to an upper end of the end effector 5', which is extended through the main member 41. A semicircular-shape second gear 44 engages the first gear 51 is fixed to side surface of one of the coupling members 42.

In this modification example, when the main member 41 of the traveling plate 4' is moved with four degrees of freedoms by suitably controlling the actuators 2, the main member 41 rotates relative to the coupling member 42. Then, as the first gear 51 fixed the end effector 5' is engaging the second gear 44 fixed the coupling member 42, the end effector 5' is rotated relative to the main member 41. Hereby, the rotational range of the end effector 5' is extended widely in comparison with the traveling plate 4 of the embodiment I.

Thus, the four-degree-of-freedom parallel robot of this modification example not only achieves substantially the same effect as in the embodiment I but also achieves the effect of rotating the end effector 5' with wider rotational range. This modification example is suited to be used as a material-handling robot, since the material-handling robot is often required to turn a material 180°.

2. Embodiment II (Construction of Embodiment II)

Figure 15:
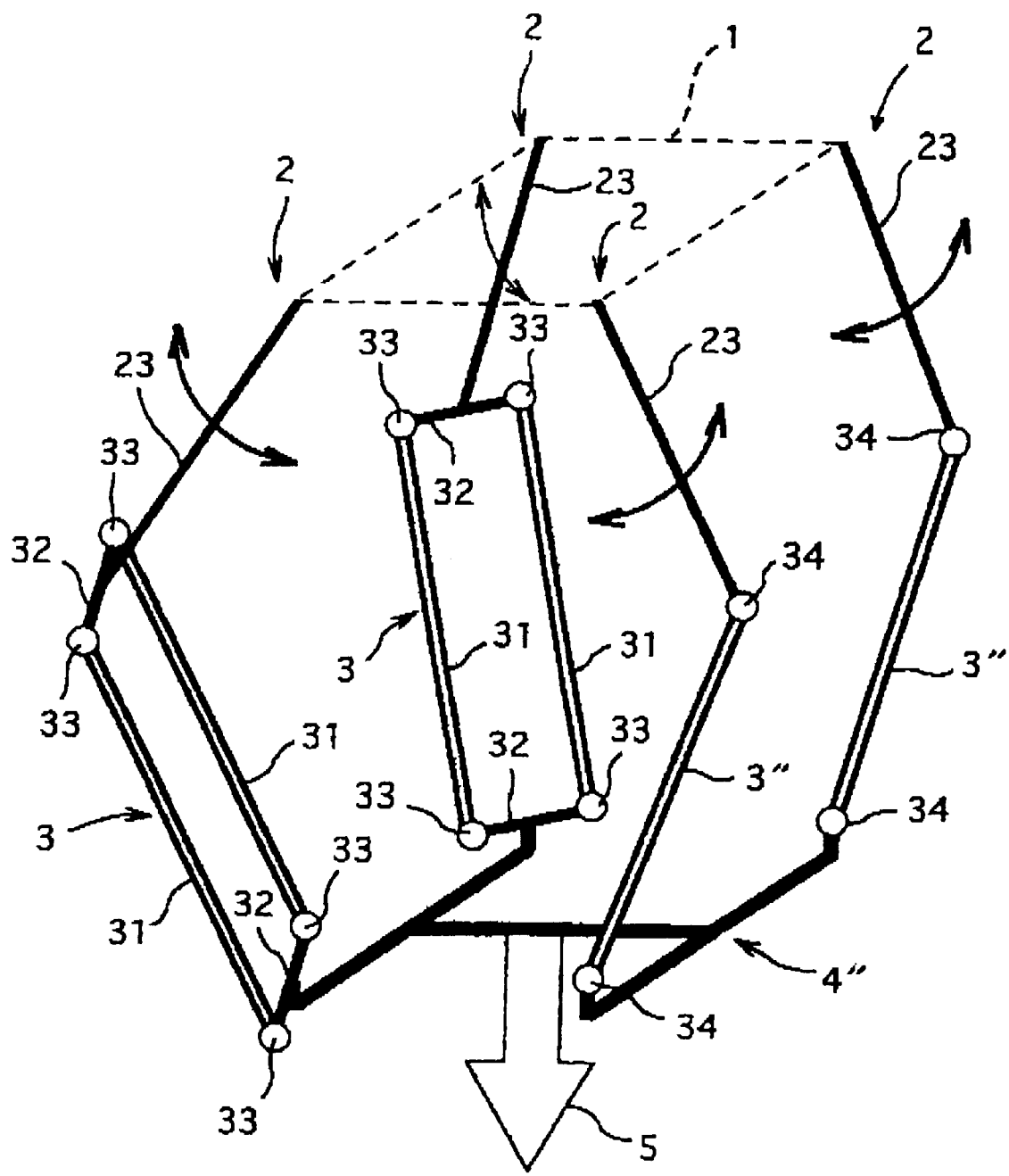
FIG. 15 is a schematic perspective view of the structure of a linkage mechanism in accordance with a second embodiment of the present invention.

As shown in FIG. 15, a four-degree-of-freedom parallel robot in accordance with embodiment II of the present invention has a construction wherein two of the four parallel linkages 3 of embodiment I are replaced by unique rods 3". The unique rods 3" are coupled at both ends to tip ends of the actuators 2 and to four corners of a traveling plate 4". Unlike the traveling plate 4 of the embodiment I, the traveling plate 4" does not have the pivots 43 and is constructed to an integral member. To facilitate comparison with the traveling plate 4 of the aforementioned embodiment I, FIG. 15 shows the traveling plate 4" in the shape of H. However, the traveling plate 4" is actually constructed of a generally rectangular and highly rigid plate.

That is, in the four-degree-of-freedom parallel robot of this embodiment, two of the rod members are the parallel linkages 3 each of which has two parallel rods 31, as is the case with the embodiment I. The end members 32 at both ends of each of the parallel linkages 3 are fixed to the actuator 2 and the traveling plate 4" respectively. The end members 32 are coupled to the rods 31 through the universal joints 33.

On the other hand, each of the other two of the rod members is designed as unique rod 3', unlike the case with the embodiment I. Ball joints 34 are provided at both ends of each rod 3". That is, each of the rods 3" is coupled at both ends to the tip end of the arm 23 of the actuator 2 and the corner portion of the traveling plate 4" through the ball joints 34. Therefore, the rods 3" are free of moment as to torsional deformation. That is, only at least one of a tensile axial force and a compressive axial force is applied to the rods 3". Hence, the rods 3" have sufficiently high rigidity for an axial force.

(Operation and Effect of Embodiment II)

In the four-degree-of-freedom parallel robot of this embodiment, two of the four rod members constitute the aforementioned parallel linkages 3, and the other two are the rods 3' which are free of moment and capable of torsional displacement because of the ball joints 34. In other words, the other two (the rods 3') of the four rod members have a degree of freedom as to torsional movement.

Thus, unlike the case with the aforementioned embodiment I, even though the traveling plate 4" is a rigid integral member, the linkage mechanism formed of the four rod members and the traveling plate 4" is not statically indeterminate. If positions of base end portions of the four rod members are determined, positions of tip end portions of the rod members are also determined uniquely in the three-dimensional space. Hence, the position and posture of the traveling plate 4" are also determined uniquely.

As a result, the traveling plate 4" can be constructed of an integral member, and two of the four rod members are simple rods. Thus, the number of parts can be reduced in comparison with the aforementioned embodiment I. Therefore, the four-degree-of-freedom parallel robot of this embodiment makes it possible to significantly improve reliability and further cut down the cost especially in the case of mass production.

The number of parts required by the four-degree-of-freedom parallel robot of this embodiment is small. Thus, in addition to the effect of the aforementioned embodiment I, the four-degree-of-freedom parallel robot of this embodiment achieves not only the effect of significantly improving reliability but also the effect of further cutting down the cost in the case of mass production.

(Respective Modification Examples of Embodiment II)

The four-degree-of-freedom parallel robot of this embodiment can also be realized in accordance with modification examples substantially identical to those of the embodiment I. Each of these modification examples makes it possible to achieve its distinctive effect. But, in the embodiment II since the traveling plate 4" does not have the pivots 43 and is constructed of an integral member, the modification example VI of the embodiment I is not able to be applied.

3. Embodiment III (Construction of Embodiment III)

Figure 16:
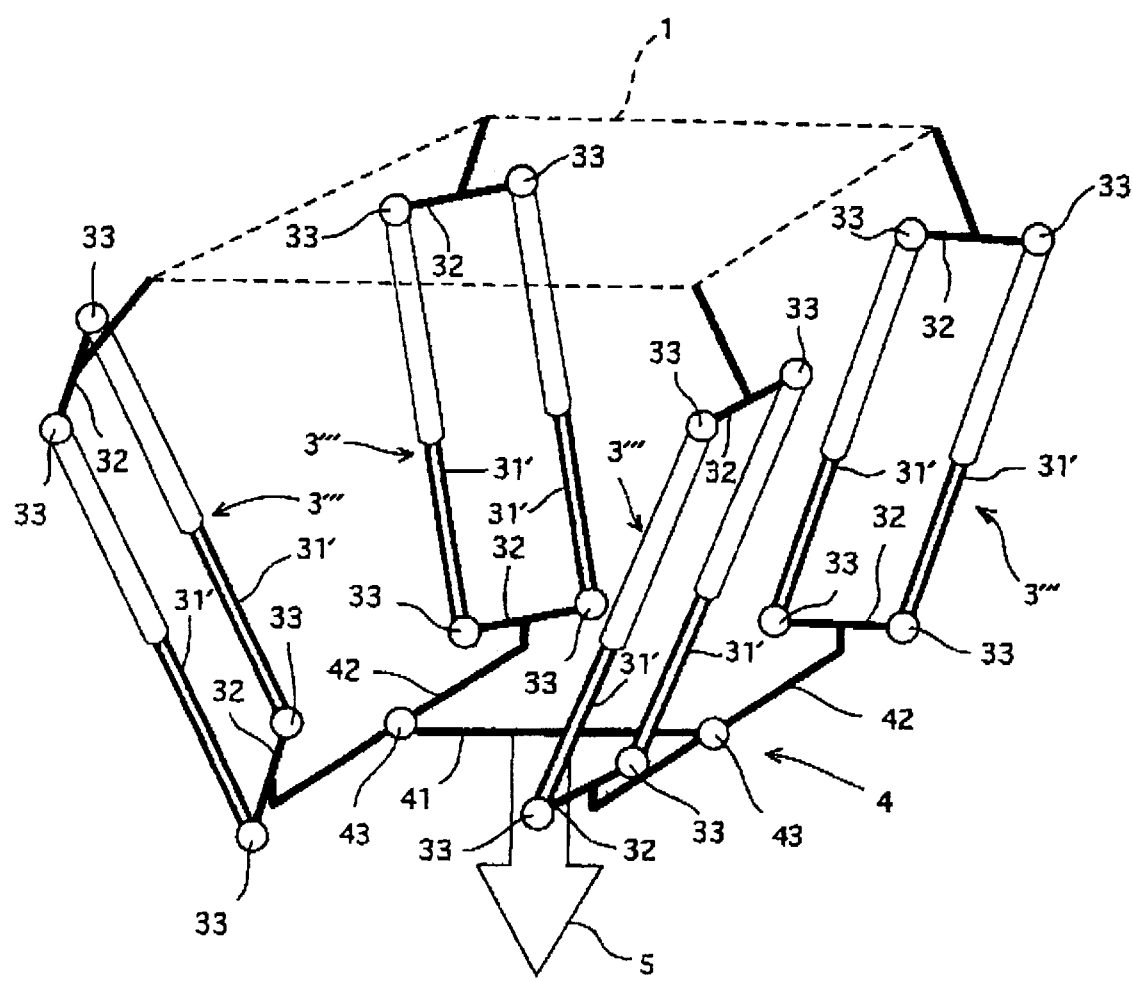
FIG. 16 is a schematic perspective view of the structure of a linkage mechanism in accordance with a third embodiment of the present invention.

As shown in FIG. 16, a four-degree-of-freedom parallel robot in accordance embodiment III of the present invention has a base 1, four actuator rods 3''' which are connected at one end to the base 1 through universal joints 33 and which can be expanded or contracted to a desire length, and traveling plate whose four corners are coupled to the actuator rods 3''' at the other end through universal joints 33.

As far as the construction of the traveling plate 4 is concerned, the four-degree-of-freedom parallel robot of this embodiment is identical to that of the embodiment I. However, the four-degree-of-freedom parallel robot of this embodiment is different from that of the embodiment I in that parallel linkages having rods 31 formed of air cylinders are disposed in place of the actuators 2 and the parallel linkages 3 fixed to the base 1 of the embodiment I.

That is, the four-degree-of-freedom parallel robot employs four parallel linkages as actuator rods. Each of the parallel linkages has a pair of air cylinders 31' which extend in parallel with each other. Each air cylinder 31' is rotatably connected at its upper end portion to a predetermined position on a lower surface of the base through a universal joint 33. On the other hand, as is the case with the rods 31 of the parallel linkages 3 of the embodiment I, each air cylinder 31' is rotatably coupled at its lower end portion to an end of the end member 32, which is fixed to an end of the coupling member 42 of the traveling plate 4 through the universal joint 33 at a predetermined angle.

The control device 6 (see FIG. 4) synchronously controls both the air cylinders 31' in each of the parallel linkages such that both the air cylinders 31' are kept equal in stroke. Each air cylinder is 31' provided with a linear potentiometer (not shown) for detecting a stroke thereof.

Therefore, as in the case with the traveling plate 4 of the embodiment I, the main member 41 of the traveling plate 4 can be displaced with four degrees of freedom. That is, the member 41 can be translated in all the directions and rotated around the vertical axis.

(Operation and Effect of Embodiment III)

As described above, the four-degree-of-freedom parallel robot of this embodiment achieves substantially the same operation and effect as in the embodiment I. However, the positioning precision of the traveling plate 4 depends largely on the precision of the linear potentiometers attached to the air cylinders 31'. Further, although implementation of feedback control can compensate for insufficient rigidity to some extent, use of the air cylinders 31' inevitably imposes a limit on rigidity.

Nevertheless, in this embodiment, there is no actuator fixed to the base, and the air cylinders 31' serving as the actuators 2 and the parallel linkages 3 of the embodiment I are employed. Hence, it is possible to simplify the overall structure and achieve a substantial reduction in size and weight. Further, since the air cylinders 31' are inexpensive actuators capable of operating at a high speed, it is possible to increase the operational speed of the traveling plate 4 and further cut down the cost.

Thus, the four-degree-of-freedom parallel robot of this embodiment achieves the effect of significantly reducing the size, weight and cost while displacing the traveling plate 4 with four degrees of freedom at a high speed.

(Modification Example I of Embodiment III)

As a modification example I of this embodiment, it is possible to realize a four-degree-of-freedom parallel robot wherein each actuator rod is composed of a hydraulic cylinder and a parallel linkage 3.

In this modification example, each actuator rod is composed of a hydraulic cylinder which is rotatably fixed at its base end to the base through a universal joint 33 and of a parallel linkage 3 having one of its end members 32 fixed to a tip end of a piston of the hydraulic cylinder.

In this modification example, the traveling plate 4 can be positioned and displaced with four degrees of freedom by merely using four hydraulic cylinders as actuators. Besides, the actuators have high rigidity. Thus, this modification example makes it possible to achieve substantially the same operation and effect as in the embodiment I.

(Modification Example II of Embodiment III)

As a modification example II of this embodiment, it is possible to realize a four-degree-of-freedom parallel robot wherein mounting angles of the end members 32 of the parallel linkages 3 have been changed or wherein the universal joints 33 have been replaced by ball joints 34.

That is, the four-degree-of-freedom parallel robots of this embodiment and its modification example I can also be realized in accordance with modification examples corresponding to the embodiment I and its modification example I. Each of these modification examples makes it possible to achieve substantially the same operation and effect.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements. In addition, while the various elements of the disclosed invention are shown in various combinations and configurations which are exemplary, other combinations and configurations, including more, less or only a single embodiment, are also within the spirit and scope of the present invention.

What is claimed is:

1. A four-degree-of-freedom parallel robot comprising:

a base;

exactly four actuators fixed to said base;

four rod members, each of which is coupled at one end to a movable portion of said actuators through a kinematic element; and a traveling member having four corners which are coupled to the other ends of said rod members through kinematic elements, wherein:

said actuators and rod members are arranged such that at least part of said traveling member can be displaced with four degrees of freedom which are defined by linear motions along three orthogonal axes and one rotation around a predetermined axis.

2. The four-degree-of-freedom parallel robot according to claim 1, wherein:

said traveling member has a main member with opposed ends serving as said part that can be displaced with four degrees of freedom and a pair of coupling members having intermediate portions which are relatively rotatably coupled to the opposed ends of said main member and whose opposed end portions are coupled to said rod members.

3. The four-degree-of-freedom parallel robot according to claim 2, wherein:

each of said rod members is constructed of two parallel rods constituting a parallel linkage; and if a predetermined direction around the axis of said rotational movement is defined as a reference direction, direction of said rod members coupled to said four corners of said traveling member are determined as one of the following combinations in one rotational direction;

a combination of 0°, 90°, 225° and 315°;

a combination of 0°, 180°, 225° and 315°;

a combination of 45°, 180°, 180° and 315°;

a combination of 0°, 135°, 180° and 315°;

a combination of 0°, 90°, 180° and 270°.

4. The four-degree-of-freedom parallel robot according to claim 2, further comprising:

an end effector attached said main member rotatably around said predetermined axis;

a first gear fixed said end effector and rotated with said end effector; and a second gear fixed said coupling member and engaged said first gear; wherein:

said end effector is rotated around said predetermined axis relative to said main member by rotation of said main member relative to said coupling member.

5. The four-degree-of-freedom parallel robot according to claim 1, wherein:

each of two of the rod members is constructed of two parallel rods constituting a parallel linkage; and each of the other two of the rod members is constructed of one rod.

6. The four-degree-of-freedom parallel robot according to claim 1, wherein:

at least one of said kinematic elements is one of a universal joint and a ball joint.

* * * * *

UNITED STATES PATENT AND TRADEMARK OFFICE
CERTIFICATE OF CORRECTION

PATENT NO. : 6,516,681 B1
DATED : February 11, 2003
INVENTOR(S) : Pierrot et al.

It is certified that error appears in the above-identified patent and that said Letters Patent is hereby corrected as shown below:

<u>Title page,</u>
Item [75], the second inventor's address is incorrect. Item [75] should read:

-- [75]  Inventors: Francois Pierrot, 120 Montee du Terral, 34430 Saint-Jean-de-Vedas (FR); Olivier Company, 11 Boulevard Pasteur, 34150 Gignac (FR); Tetsuro Shibukawa, Nagoya (JP); Koji Morita, Kariya (JP) --

Signed and Sealed this

Twenty-fourth Day of June, 2003

JAMES E. ROGAN
*Director of the United States Patent and Trademark Office*